United States Patent [19]

Phillipps et al.

[11] Patent Number: 4,515,786
[45] Date of Patent: May 7, 1985

[54] 11α-AMINO-ANDROSTANES

[75] Inventors: Gordon H. Phillipps, Wembley; David C. Humber, Ealing; George B. Ewan, Northolt; Barry A. Coomber, Pinner, all of England

[73] Assignee: Glaxo Group Limited, London, England

[21] Appl. No.: 509,667

[22] Filed: Jun. 30, 1983

Related U.S. Application Data

[63] Continuation of Ser. No. 383,338, May 28, 1982, abandoned.

[30] Foreign Application Priority Data

May 29, 1981 [GB] United Kingdom ............... 8116409

[51] Int. Cl.³ ................................. C07J 3/00
[52] U.S. Cl. .................. 514/182; 260/397.1; 260/397.45
[58] Field of Search ............. 260/397.1; 424/238

[56] References Cited

U.S. PATENT DOCUMENTS 3,989,686 11/1976 Phillipps et al. ............. 260/397.1
4,197,296  4/1980 Phillipps et al. ............. 260/397.1
4,352,798 10/1982 Phillipps et al. ............. 260/397.1

FOREIGN PATENT DOCUMENTS 2715078 10/1977 Fed. Rep. of Germany ... 260/397.1

Primary Examiner—Elbert L. Roberts

Attorney, Agent, or Firm—Bacon & Thomas

[57] ABSTRACT

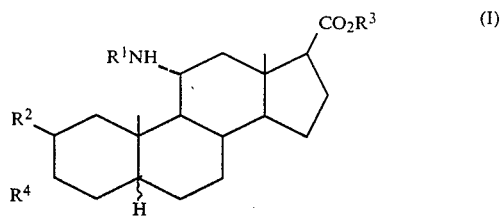

wherein $R^1$ is a $C_{1-8}$ alkyl group or a $C_{3-7}$ cycloalkyl group;
$R^2$ is a hydrogen atom, a $C_{1-6}$ alkoxy group or a $C_{2-5}$ alkanoyloxy group;
$R^3$ is a $C_{1-6}$ alkyl group or a $C_{3-7}$ cycloalkyl group; and
$R^4$ is a group $-OR^5$ or $-OCOR^6$ where
$R^5$ is an optionally substituted alkyl or alkenyl group which may contain up to 6 carbon atoms, an optionally substituted $C_{3-7}$ cycloalkyl group, a phenyl group or a carbon-attached 5–7 membered heterocyclic ring in which the hetero-atom is selected from nitrogen, oxygen and sulphur, and
$R^6$ is a hydrogen atom or a group $R^5$ as defined above;
provided that when the compounds contain a 5β-hydrogen atom, $R^2$ is a hydrogen atom and salts thereof, which compounds have activity as antidysthythmic agents.

15 Claims, No Drawings

11α-AMINO-ANDROSTANES

This application is a continuation of application Ser. No. 383,338 filed May 28, 1982, now abandoned.

This invention relates to aminosteroids having antidysrhythmic activity, and in particular to certain compounds in the androstane series having a substituted amino group at the 11α-position.

The aim of antidysrhythmic therapy is to return hazardous abnormal heart rhythms towards normal, or to reduce the likelihood of hazardous rhythms developing in patients at risk as a result of hypertension, atheromas, diabetes or heart conditions such as myocardial disease, ischaemia or infarction.

It is recognised that dysrhythmias in patients with heart attack and other conditions are treatable and preventable. There are several drugs available for the treatment of ventricular dysrhythmias but their application is limited by their lack of efficacy or by their toxicity which gives rise to various side effects.

Thus there is a demand for drugs suitable for use in the treatment of patients with dysrhythmias, and therefore in danger of sudden cardiac death. Furthermore, there is a demand for such drugs for administration, for example for long term prophylaxis, to patients at risk of developing dysrhythmias, in which case, activity on oral administration is desirable.

In Belgian Patent Specification No. 853227 there is described a group of 11α-tertiary amino-3α-hydroxy steroids having anaesthetic activity. In addition to the 11α-tertiary amino and 3α-hydroxy groups, the possibility of the compounds possessing various substituents in other positions including the 17β-position is allowed for, one possible 17β-substituent being a $C_{1-5}$ alkoxycarbonyl group. Corresponding 11α-primary and secondary amino steroids are also described as intermediates for the preparation of the tertiary amino compounds. There is no specific disclosure in Belgian Pat. No. 853227 of any 11α-primary or secondary amino-17β-alkoxycarbonyl compounds, and no anaesthetic activity is ascribed to any such compounds specifically. Moreover, there is no disclosure whatsoever in Belgian Pat. No. 853227 of any 3α-ester or ether 11α-primary or secondary amino 17β-carboxylate compounds. Furthermore, no antidysrhythmic activity has been ascribed to any of the compounds in the above Belgian Patent Specification, or indeed to any compounds of comparable structure.

We have now discovered that a group of steroids having a primary or secondary amino group at the 11α-position and a 3α-ester or ether group have promising antidysrhythmic activity.

Accordingly the invention provides 11α-aminoandrostanes of the formula

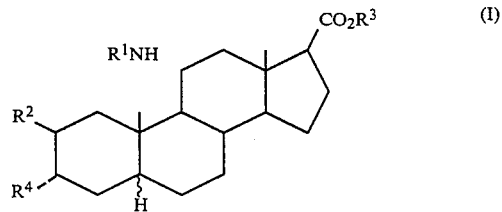

(I)

wherein $R^1$ is a $C_{1-8}$ alkyl group or a $C_{3-7}$ cycloalkyl group;

$R^2$ is a hydrogen atom, a $C_{1-6}$ alkoxy group or a $C_{2-5}$ alkanoyloxy group;

$R^3$ is a $C_{1-6}$ alkyl group or a $C_{3-7}$ cycloalkyl group; and $R^4$ is a group —$OR^5$ or —$OCOR^6$ where $R^5$ is an alkyl or alkenyl group which may contain up to 6 carbon atoms (or such a group substituted by halogen, $C_{1-6}$ alkoxy (e.g. methoxy or ethoxy), carboxy, phenyl or phenyl substituted by nitro, halo, $C_{1-4}$ alkoxy (e.g. methoxy) or $C_{1-4}$ alkyl (e.g. methyl)), a $C_{3-7}$ cycloalkyl group, a phenyl group (or such a group substituted by nitro, halo, $C_{1-4}$ alkoxy (e.g. methoxy) or $C_{1-4}$ alkyl (e.g. methyl)), or a carbon-attached 5–7 membered heterocyclic ring in which the heteroatom is selected from nitrogen, oxygen and sulphur, and $R^6$ is a hydrogen atom or a group $R^5$ as defined above; provided that when the compounds contain a 5β-hydrogen atom, $R^2$ is a hydrogen atom;

and the D-homo analogues thereof having the group —$CO_2R^3$ (wherein $R^3$ is defined above) at the 17aβ-position, and salts thereof.

The compounds of the invention have been found to possess useful antidysrhythmic activity in the tests which have been carried out, and have potential as antidysrhythmic drugs.

The 5-hydrogen atom may be in the α- or β-configuration.

Where one of the groups $R^1$, $R^3$, $R^5$ or $R^6$ is an alkyl group it may be a straight or branched chain group.

Where $R^1$ is a cycloalkyl group, it may be, for example, a cyclobutyl, cyclopentyl, cyclohexyl or cycloheptyl group.

Where $R^1$ is an alkyl group it preferably has 3–7 carbon atoms, and may, for example, be a propyl, butyl, pentyl, isopentyl, hexyl, isohexyl or neohexyl group.

Where $R^2$ is an alkoxy group it may be, for example, a methoxy, ethoxy, propoxy, butoxy, pentyloxy or hexyloxy group. An example of an alkanoyloxy group is the acetoxy group.

Where $R^3$ is a cycloalkyl group it may be, for example, a cyclopropyl, cyclobutyl, cyclopentyl or cyclohexyl group. Where $R^3$ is an alkyl group, it may be, for example, a methyl, ethyl, propyl, isopropyl, butyl or isopentyl group. $R^3$ is advantageously a $C_{1-3}$ alkyl group.

Where $R^5$ or $R^6$ is an alkyl or alkenyl group, it may, for example, be a methyl, ethyl, propyl or propenyl group. Where $R^5$ or $R^6$ is substituted there will generally be one such substituent except in the case of halogen substituents where there may be, for example, 1–3 substituents. Examples of suitable halogen substituents are fluoro, chloro and bromo.

Where $R^5$ or $R^6$ is a carbon-attached heterocyclic group it may be saturated or unsaturated, containing up to 3 double bonds. Examples of such groups include tetrahydropyranyl, tetrahydrofuranyl, furyl, thienyl and pyridyl.

Where compounds having good activity following oral administration are desired, $R^3$ is preferably a methyl or ethyl group.

Particularly preferred compounds are those in which $R^1$ is an isopentyl, hexyl, isohexyl, neohexyl, cyclopentyl or cyclohexyl group; $R^2$ is a hydrogen atom or a methoxy, ethoxy or propoxy group; $R^3$ is a methyl or ethyl group, especially a methyl group; and $R^4$ is a methoxy, ethoxy or acetoxy group. The compounds preferably contain a 5α-hydrogen atom.

Ring D conveniently has 5 members.

The compounds of formula (I) and D-homo analogues thereof may form acid addition salts; physiologically acceptable acid addition salts are preferred. Those compounds in which the group $R^4$ contains a carboxy group may also form salts with bases or exist in zwitterionic forms. The term "salts" is used herein, unless otherwise specified, to designate acid addition salts, base salts and zwitterionic forms.

Examples of acid addition salts are hydrochlorides, hydrobromides, phosphates, sulphates, p-toluenesulphonates, methanesulphonates, citrates, tartrates, acetates, ascorbates, lactates, maleates, succinates, tricarballylates, glutarates and glutaconates. The hydrochlorides are preferred acid addition salts. The salts with bases may be salts with inorganic bases such as alkali metal salts, e.g. sodium, potassium and lithium salts; alkaline earth metal salts, e.g. calcium and magnesium salts; and ammonium salts, or salts with inorganic bases, e.g. amine salts.

Individual compounds which are preferred on the basis of their high antidysrhythmic activity include:
1. Ethyl 3α-acetoxy-2β-ethoxy-11α-(3-methylbutylamino)-5α-androstane-17β-carboxylate;
2. Methyl 3α-acetoxy-2β-ethoxy-11α-(3-methylbutylamino)-5α-androstane-17β-carboxylate;
3. Methyl 2β,3α-diethoxy-11α-(3-methylbutylamino)-5α-androstane-17β-carboxylate;
4. Methyl 11α-cyclohexylamino-2β,3α-diacetoxy-5α-androstane-17β-carboxylate;
5. Methyl 3α-acetoxy-11α-cyclohexylamino-5α-androstane-17β-carboxylate;
6. Methyl 3α-acetoxy-11α-cyclohexylamino-2β-methoxy-5α-androstane-17β-carboxylate;
7. Methyl 2β,3α-diacetoxy-11α-(3-methylbutylamino)-5α-androstane-17β-carboxylate;
8. Methyl 3α-acetoxy-11α-(3-methylbutylamino)-5α-androstane-17β-carboxylate; and
9. Methyl 3α-ethoxy-11α-(3-methylbutylamino)-5α-androstane-17βcarboxylate;
and their physiologically acceptable acid addition salts, e.g. their hydrochlorides.

The invention further provides compounds of formula (I), D-homo analogues thereof and physiologically acceptable salts thereof for use in a method of treatment of the human or animal, in particular mammalian, body to combat cardiac dysrhythmias therein. The invention also provides compounds of formula (I), D-homo analogues thereof and physiologically acceptable salts thereof in association with instructions for their use as antidysrhythmic agents.

The compounds may be used in the treatment of patients with disturbances of cardiac rhythm, whether arising spontaneously, or as a result of treatment with other drugs, e.g. cardiac glycosides, or as a consequence of myocardial ischaemia or infarction. Alternatively they may be used for the prophylactic treatment of patients at risk of cardiac rhythm disturbances or sudden coronary death.

Accordingly, the invention provides methods of therapy or prophylaxis of a human or animal, in particular mammalian, body suffering from or liable to cardiac dysrhythmias which method comprises, administering to the said body an effective amount of a compound of formula (I), a D-homo analogue thereof or a physiologically acceptable salt thereof.

As a further aspect of the invention there are provided compounds of the formula

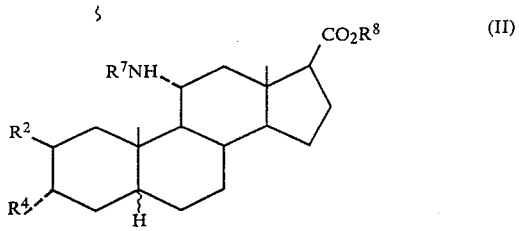

wherein $R^7$ is a hydrogen atom, a $C_{1-8}$ alkyl group or a $C_{3-7}$ cycloalkyl group; $R^8$ is a hydrogen atom, a $C_{1-6}$ alkyl group or a $C_{3-7}$ cycloalkyl group; and $R^2$ and $R^4$ are as hereinbefore defined; with the provisos that at least one of $R^7$ and $R^8$ is a hydrogen atom and that when the compounds contain a 5β-hydrogen atom $R^2$ is a hydrogen atom; and the D-homo analogues thereof having the group —$CO_2R^8$ (wherein $R^8$ is as defined above) at the 17aβ-position, and salts and zwitterionic forms thereof.

The compounds of formula (II) and the D-homo analogues thereof may form acid addition salts. Those compounds in which the group —$CO_2R^8$ represents a carboxyl group may also form salts with bases or exist as zwitterions.

Examples of salts are those given above in connection with the compounds of formula (I).

Compounds of formula (II) and the D-homo analogues thereof are useful as intermediates in the preparation of compounds of formula (I) or the D-homo analogues thereof using the methods described hereinafter.

The compounds of the invention may be prepared by a number of different methods, using generally known techniques. Suitable methods are described below:

1. A substituent on the 11α-amino function may be introduced by reacting the corresponding 11α-amino compound, i.e. a compound of formula (II) in which $R^7$ is hydrogen, with a compound of the formula $R^1X$ wherein X is a readily displaceable atom or group such as halide (e.g. iodide), a hydrocarbylsulphonyloxy group (e.g. toluene-p-sulphonyloxy), a hydrocarbyloxysulphonyloxy group (e.g. methoxysulphonyloxy) or a dialkoxyphosphonyloxy group (e.g. dimethoxyphosphonyloxy). When carried out on compounds of formula (II) in which $R^8$ is also hydrogen, such a reaction may result in esterification to form a compound in which $R^1=R^3$. The group $R^3$ may, if not desired in the final product, subsequently be replaced by transesterification, for example as set out under 6 below. However, where $R^8$ is hydrogen and the initial product is a carboxylic acid, this should be esterified for example as set out under 4 below. The introduction of the substituent on the 11α-amino function is preferably carried out in the presence of a base (e.g. potassium carbonate or silver oxide) in solution at any suitable temperature from ambient to reflux (e.g. +20° to +100° C.) The reaction is conveniently effected in a suitable reaction solvent. Suitable solvents include ethers (e.g. dioxan), substituted amides (e.g. N,N-dimethylformamide or N,N-dimethylacetamide), sulphoxides (e.g. dimethylsulphoxide), alkanols (e.g. ethanol or methanol) or acetonitrile.

When X is a chlorine or bromine atom, the reaction may be facilitated by addition of an iodide such as sodium iodide.

Compounds of formula (II) wherein $R^7$ is hydrogen may be prepared by reduction of the corresponding 11-oxime. Such a reduction may be effected with an alkali or alkaline earth metal in an alcohol and/or an amine and/or ammonia, e.g. sodium in n-propanol, if desired in the presence of a suitable solvent, e.g. tetrahydrofuran, at any suitable temperature up to and preferably at reflux.

The 11-oximes may themselves be prepared from the corresponding 11-oxo compounds. The 11-oxo compound may for example be reacted with hydroxylamine under strongly alkaline conditions in aqueous alcohol (e.g. ethanol), preferably at reflux. The reaction may also be carried out under acidic conditions (ca. pH 4), e.g. in buffered pyridine.

The severe conditions used in the reduction of the 11-oxime make it necessary or desirable that certain substituents for example the $17\beta$-alkoxycarbonyl substituent, the $3\alpha$-ester substituent and the $2\beta$-alkanoyloxy substituent should be introduced after the formation of the $11\alpha$-amino group.

2. A corresponding $11\alpha$-amino compound, i.e. a compound of formula (II) in which $R^7$ is hydrogen, can be reductively "alkylated" with an appropriate monocarbonyl compound in the presence of a reducing agent, the term "alkylated" being used to refer to the introduction of a cycloalkyl group as well as an alkyl group. The reducing agents which may be used are those generally known for the reduction of imines, examples being formic acid (e.g. at any suitable temperature up to 100°–120° C., for example from room temperature up to 100°, and using the carbonyl compound as the reaction solvent, in the presence or absence of water), an alkali metal borohydride or cyanoborohydride (e.g. sodium borohydride or cyanoborohydride, using an alcohol such as ethanol as solvent, suitably at room temperature), iron pentacarbonyl or an alkali metal hydrogen iron carbonylate (e.g. Fe(CO)$_5$ or MHFe(CO)$_4$ where M is sodium or potassium, at any suitable temperature up to reflux using an ether such as tetrahydrofuran or an alcohol or aqueous alcohol as solvent), hydrogen in the presence of a metal catalyst (using an alcohol, e.g. ethanol, an ether, e.g. dioxan or an ester, e.g. ethyl acetate, as reaction solvent, conveniently at room temperature), or aluminium amalgam in the presence of water (conveniently at room temperature, and in the presence of an ether solvent such as tetrahydrofuran).

The metal catalyst may, for example, be a noble metal catalyst such as platinum, platinum oxide, palladium or rhodium. The catalyst may be supported, e.g. on charcoal or kieselguhr. A homogeneous catalyst such as tristriphenylphosphine rhodium chloride may also be used. If desired the intermediate imino compound may be isolated. Thus, for example, the use of formaldehyde, acetaldehyde, 3-methylbutanal or cyclohexanone can provide the $11\alpha$-N-methyl, N-ethyl, N-iso-pentyl or N-cyclohexyl amines respectively.

It will be appreciated that the conditions should be chosen to give predominantly the desired N-monosubstituted compound, and minimise production of the corresponding N,N-disubstituted compound. Reductive alkylation of the compounds of formula (II) in which $R^8$ is a hydrogen atom is preferably effected under basic conditions.

Where $R^8$ is hydrogen, the initial product will be a carboxylic acid which should then be esterified to form an ester according to the invention, for example as set out in 4 below.

3. Conversion of a N,N-disubstituted $11\alpha$-amine into a N-mono-substituted compound.

Compounds of formula (I) can be prepared from corresponding $11\alpha$-tertiary amino compounds by replacement of one of the groups by a hydrogen atom, e.g. by dealkylation using for example sodium nitrite followed by catalytic hydrogenolysis.

Thus, in particular, the compounds may be prepared by deprotection of a corresponding $11\alpha$-(protected amino) compound, having a substituent $R^1$ in addition to the protecting group, which may be, for example an acyl group such as a trichloroethoxycarbonyl, trifluoroacetyl, formyl or silyl, e.g. trimethylsilyl, group. An acyl group may be removed by hydrolysis e.g. with acid or alkali. The trichloroethoxycarbonyl group may also be removed by reduction with, for example, zinc and acetic acid. Alternatively an arylmethyl protecting group such as a benzyl group may be removed by catalytic hydrogenation to produce the unprotected $11\alpha$-mono-substituted amino compound. A silyl group may be removed by e.g. solvolysis, with water (optionally containing acid or base) or an alcohol, or by treatment with a fluoride such as tetrabutylammonium fluoride.

This method may also be used to prepare compounds of formula (II) in which $R^7$ is hydrogen, by deprotection of a corresponding $11\alpha$-(protected amino) compound to yield a free $11\alpha$-amino group.

4. Esterification of a corresponding $17\beta$-carboxylic acid.

Compounds of formula (I) may be prepared by reacting the corresponding compound of formula (II) in which $R^8$ is hydrogen or a reactive derivative thereof (e.g. an acid halide or anhydride or a salt) with the appropriate alcohol or alkyl or cycloalkyl halide. This reaction is preferably carried out at temperatures of $-20°$ C. to $+110°$ C., as is described for example in our British Patent Specification No. 1,380,246.

Where an alcohol is used in the esterification reaction, a coupling agent may be employed, for example a carbodiimide such as dicyclohexylcarbodiimide, preferably in the presence of a catalyst such as 4-dimethylaminopyridine.

Alternatively, esterification may be effected using a diazoalkane such as diazomethane.

Compounds of formula (II) in which $R^8$ is hydrogen can conveniently be formed by oxidising the corresponding $17\beta$-acetyl compound, i.e. a pregnan-20-one, using for example NaOBr in an aqueous inert solvent (e.g. dioxan).

Compounds of formula (II) in which $R^8$ is a hydrogen atom and $R^4$ is a group $-OR^5$ may be prepared from their corresponding esters, for example by hydrolysis under acidic or basic conditions. Examples of suitable acids for such hydrolysis include mineral acids such as hydrochloric acid; examples of suitable bases include alkali metal hydroxides and carbonates, such as sodium or potassium hydroxides or carbonates.

When using certain of the above reagents, for example alkyl halides, it may be necessary to protect the $11\alpha$-amino group, for example as a trichloroethoxycarbonyl derivative.

5. Reduction of a corresponding $\Delta^{16}$-compound. The reduction may be effected by hydrogenation in the presence of a catalyst (e.g. a palladium catalyst) in a suitable solvent (e.g. an alcohol, ether or ester). The reaction may be effected conveniently at or about room temperature and atmospheric pressure in the presence of a tertiary base, e.g. triethylamine, and/or an acid, e.g. acetic acid.

The starting materials may be prepared by reaction of the corresponding 17-oxo compound with aqueous hydrogen cyanide to produce the 17-cyanohydrin which may be dehydrated to produce the $\Delta^{16}$-17$\beta$-cyano compound. This yields on hydrolysis the $\Delta^{16}$-17$\beta$-carboxylic acid and on alkylation, the corresponding $\Delta^{16}$-17$\beta$-ester.

6. Compounds of formula (I) in which $R^4$ is a group $—OR^5$ may also be prepared by transesterification i.e. by reaction of a corresponding compound having a 17$\beta$-ester group with an alcohol of formula $R^3OH$ in the presence of an acid or base catalyst at any temperature from room temperature to reflux, conveniently from 50° to 100° C., so as to produce a compound of formula (I) having a different 17$\beta$-ester group from the starting material; normally an excess of alcohol is used. Examples of suitable acid catalysts include mineral acids e.g. sulphuric and hydrochloric, and examples of suitable base catalysts include alkali metal hydroxides and carbonates, e.g. sodium or potassium hydroxides or carbonates.

7. Esterification or etherification of the corresponding 3$\alpha$-hydroxy compound.

The 3$\alpha$-esters according to the invention may be prepared from the corresponding 3$\alpha$-hydroxy compounds using conventional acylation techniques. Thus, the 3$\alpha$-hydroxy compound may be reacted with the appropriate acyl halide (e.g. chloride) or anhydride. The reaction is desirably effected in the presence of an acid such as toluene-4-sulphonic acid. Suitable reaction solvents include halogenated hydrocarbons such as chloroform, ethers such as tetrahydrofuran and amides such as dimethylformamide.

The 3$\alpha$-ethers according to the invention may be prepared by reacting the corresponding 3$\alpha$-hydroxy compounds with an etherifying agent. Etherifying agents which may be used include dimethyl sulphate compounds of the formula $R^5Y$ (where $R^5$ is as defined above and Y is a readily displaceable atom or group, such as a halide (e.g. chloride or iodide) or hydrocarbylsulphonyloxy (e.g. methanesulphonyloxy) group), and diazo reagents, such as diazoalkane or diazoaralkane, preferably in the presence of a Lewis acid such as boron trifluoride. When esterification is effected using a compound of formula $R^5Y$ (where $R^5$ is as defined above and Y is a halide), the reaction may be assisted by the use of silver oxide. The reaction may be effected in a solvent such as an ether e.g. dioxan or tetrahydrofuran, a hydrocarbon e.g. a light petroleum fraction, or a halogenated hydrocarbon e.g. chloroform.

Etherification may also be carried out by reaction of the 3$\alpha$-hydroxy compound with a vinyl ether. This method may be used to prepare tetrahydropyranyl ethers, using dihydropyran as reagent, or 1-alkoxyalkyl ethers, using an alkyl vinyl ether as reagent. The reaction is desirably carried out in the presence of a strong acid catalyst such as sulphuric acid or toluene-4-sulphonic acid. Suitable solvents include ethers, hydrocarbons and halogenated hydrocarbons as described above.

In both the etherification and esterification reactions carried out on a compound of formula (I) it may be necessary or desirable to protect the 11$\alpha$-amine group. The protecting groups may be removed as described in process 3 above.

8. Esterification or etherification of a 2$\beta$-hydroxy compound.

Compounds of formula (I) in which $R^2$ is a $C_{1-6}$ alkoxy or $C_{2-5}$ alkanoyloxy group may also be prepared by reacting the corresponding 2$\beta$-hydroxy compound with an esterifying or etherifying agent serving to introduce the appropriate group $R^2$. Suitable esterifying and etherifying agents are described in process 7 above.

The 3$\alpha$-ester or ether-2$\beta$-hydroxy starting materials may be prepared by reacting the corresponding 2$\beta$, 3$\beta$-epoxide with a compound $HR^4$ (where $R^4$ is as defined above) under acidic conditions. The 2$\beta$, 3$\beta$-epoxide may be prepared from the corresponding 3$\alpha$-bromo-2$\beta$-hydroxy compound by treatment with a base.

9. Salt formation.

Acid addition salts may be prepared by reaction of the free base with a suitable acid.

Base salts of compounds of formula (I) wherein $R^4$ contains a carboxy group or of formula (II) wherein $R^8$ is hydrogen may be prepared by the reaction of the free acid with a suitable base. For example, alkali metal salts may be prepared by reaction with an alkali metal hydroxide, carbonate, bicarbonate or 2-ethylhexanoate.

The methods indicated above for preparing the compounds of the invention can be used as the last main step in a preparative sequence. The same general methods can be used for the introduction of the desired groups at an intermediate stage in the stepwise formation of the required compound, and it will be appreciated that these general methods can be combined in many different ways in such multi-stage processes. Thus for example the desired 11$\alpha$-amino group may be formed either before or after the introduction of the desired 3$\alpha$-ether or ester group. The sequence of the reactions in multi-stage processes should of course be chosen so that the reaction conditions used do not affect groups in the molecule which are desired in the final product.

The D-homo analogues of the compounds of the invention having a group $—CO_2R^3$ or $—CO_2R^8$ at the 17a$\beta$-position may be prepared by essentially similar methods, using appropriate starting materials of the required structure.

The 3$\alpha$-hydroxy steroids corresponding to the compounds of the invention, and which may be used as starting materials in certain of the processes set out above, may also be prepared as described in British Patent Specification No. 2080308A.

The compounds of formula (I), their D-homo analogues, and physiologically acceptable salts thereof may be formulated for administration in any convenient way, and the invention therefore includes within its scope pharmaceutical compositions comprising a compound of formula (I), a D-homo analogue thereof or a physiologically acceptable salt thereof in admixture with pharmaceutical carries or excipients.

The compounds and their physiologically acceptable salts may for example be presented in a form suitable for absorption by the gastro-intestinal tract. Tablets and capsules for oral administration may be in unit dose presentation form, and may contain conventional excipients such as binding agents, for example syrup, acacia, gelatin, sorbitol, tragacanth, mucilage of starch or polyvinylpyrrolidone; fillers, for example lactose, sugar, maize-starch, calcium phosphate or sorbitol; lubricants, for example magnesium stearate, talc, polyethylene glycol or silica; disintegrants, for example potato starch of sodium starch glycollate; or acceptable wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example sorbitol syrup, methyl cellulose, glucose-/sugar syrup, gelatin, hydroxyethylcellulose, carboxymethyl cellulose, aluminium stearate gel or hydrogenated edible fats; emulsifying agents, for example lecithin, sorbitan mono-oleate or acacia; non-aqueous vehicles (which may include edible oils), for example almond oil, fractionated coconut oil, oily esters, propylene glycol or ethyl alcohol; and preservatives, for example methyl or propyl p-hydroxybenzoates or sorbic acid. The compounds or their salts may also be formulated as suppositories, e.g. containing conventional suppository bases such as cocoa butter or other glycerides.

The compounds of formula (I), their D-homo analogues, and physiologically acceptable salts thereof may also be formulated for injection and may be presented in unit dose form in ampoules, or in multi-dose containers with an added preservative. The compositions may take such foams as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

When the compositions comprise dosage units, each unit will preferably contain 10–1000 mg of the active ingredient advantageously 25–500 mg. The daily dosage as employed for adult human treatment will preferably range from 25–2500 mg preferably 50–1000 mg depending on the route and frequency of administration. The compounds may be given in divided doses, for example 1–4 times per day.

The antidysrhythmic compounds according to the invention may be administered in combination with other therapeutic agents.

The following Examples illustrate the invention.

Melting points were determined in capillaries and are corrected. Optical rotations were determined at room temperature on 1% solutions in chloroform.

Preparative t.l.c. and column chromatography were carried out on silica.

Petrol refers to petroleum ether b.p. 60°–80° C.

Solutions were dried using anhydrous sodium sulphate.

IR spectra were determined in bromoform and refer to the carbonyl stretching frequency of the 17$\beta$-carboxylic acid ester group.

Chloroiridic acid reagent was prepared by refluxing a mixture of chloroiridic acid (50 mg), isopropanol (94 ml), water (6 ml) and trimethylphosphite for 24 hours and adjusting to pH7 by the addition of triethylamine immediately prior to use.

INTERMEDIATE 1

2$\beta$-Ethoxy-3$\alpha$-hydroxy-11$\alpha$-(2,2,2-trichloroethoxycarbonylamino)-5$\alpha$-pregnan-20-one 2$\beta$-Ethoxy-11$\alpha$-(2,2,2-trichloroethoxycarbonyloxy)-5$\alpha$-pregnan-20-one (15.5 g) in dioxan (120 ml) was treated with 2N sodium hydroxide (80 ml) for 3 h. Water (300 ml) was added and the mixture extracted with dichloromethane (3×). The extract was washed with water (2×), dried and evaporated to give the title compound (12.2 g).

INTERMEDIATE 2

2$\beta$,3$\alpha$-Diethoxy-11$\alpha$-(2,2,2-trichloroethoxycarbonylamino)-5$\alpha$-pregnan-20-one Intermediate 1 (12.082 g) and silver (I)oxide (36 g) in ethyl iodide (200 ml) were stirred and heated to reflux. After 6.5 h the reaction mixture was allowed to cool, filtered and evaporated to given an oil (14.77 g). This was purified by column chromatography in ethyl acetate/Petrol (1:3) to give a foam (4.0 g). A sample (300 mg) was crystallised from petrol to give the title compound (225 mg) m.p. 68°–71°, $[\alpha]_D$+42.7°.

INTERMEDIATE 3

2$\beta$,3$\alpha$-Diethyl-11$\alpha$-(2,2,2-trichloroethoxycarbonylamino)-5$\alpha$-androstane-17$\beta$-carboxylic acid Bromine (1.65 ml) was added to a solution of sodium hydroxide (4.63 g) in water (36 ml) keeping the temperature at −5°. Dioxan (18 ml) was added and the mixture added slowly to a stirred solution of Intermediate 2 (4.265 g) in dioxan (120 ml) and water (36 ml) at 8°. The mixture was stirred for 2.5 h, $Na_2SO_3$ (1 g) was added and the reaction mixture stirred for 15 min. Water (50 ml) and concentrated hydrochloric acid were added to pH2. The suspension was extracted with chloroform (3×). The extracts were washed with water, dried and evaporated to give an oil. This was purified by column chromatography eluted with ethyl acetate/petrol (1:3) to give the title compound (2.778). A portion was crystallised from petrol, m.p. 124°–129° $[\alpha]_D$+21.3°.

INTERMEDIATE 4

Methyl 2$\beta$,3$\alpha$-diethoxy-11$\alpha$-(2,2,2-trichloroethoxycarbonylamino)-5$\alpha$-androstane-17$\beta$-carboxylate A solution of Intermediate 3 (2.914 g) in DMF (50 ml) was stirred with $K_2CO_3$ (2.8 g) at 0°. Methyl iodide (1.9 ml) was added and stirred for 2 h. Water (200 ml) was added and extracted with ethyl acetate (3×). The extract was washed with brine (1×), dried and evaporated to give an oil . This was purified by column chromatography eluted with ethyl acetate/petrol (1:3) to give the title compound (2.703 g), $[\alpha]_D$+24.6° $\nu_{max}$ 1730 cm$^{-1}$.

INTERMEDIATE 5

Ethyl 3$\alpha$-acetoxy-2$\beta$-ethoxy-11$\alpha$-(2,2,2-trichloroethoxycarbonylamino)-5$\alpha$-androstane-17$\beta$-carboxylate Ethyl 2$\beta$-ethoxy-3$\alpha$-hydroxy-11$\alpha$-(2,2,2-trichloroethoxy-carbonylamino)-5$\alpha$-androstane-17$\beta$-carboxylate (1.83 g) in pyridine (6 ml) was treated with acetic anhydride. After b 18 h. the reaction mixture was diluted with ethanol and evaporated to give a foam (1.91 g). A portion was purified by preparative t.l.c. in ethyl acetate/Petrol (1:2) to give the title compound, $[\alpha]_D$+30.7°, $\nu_{max}$ 1724 cm$^{-1}$.

INTERMEDIATE 6

Methyl 11$\alpha$-amino-2$\beta$,3$\alpha$-diethoxy-5$\alpha$-androstane-17$\beta$-carboxylate A solution of Intermediate 4 (2.403 g) in glacial acetic acid (50 ml) was stirred with zinc (4.8 g) for 18 h. The zinc was removed by filtration and washed with water (150 ml). The filtrate and washings were brought to pH

INTERMEDIATE 7

Ethyl 3α-acetoxy-11α-amino-2β-ethoxy-5α-androstane-17β-carboxylate

Zinc powder (1.7 g) was added to a stirred solution of Intermediate 5 (1.71 g) in glacial acetic acid (34 ml). After 18 h the zinc was removed by filtration and washed with dichloromethane. The filtrate was evaporated, the residue diluted with ammonia solution and then extracted with ethyl acetate (3×). These extracts were washed with water, dried and evaporated to give a foam. This was dissolved in ethyl acetate and the resulting solution extracted with dilute hydrochloric acid (3×). These acid extracts were basified with b 0.88 NH$_3$ solution and extracted with ethyl acetate (3×). These extracts were washed with water, dried and evaporated to give a foam. This was crystallised from ether/petrol to give the title compound (168 mg), m.p. 140°–142°, $[α]_D$+48.3°.

INTERMEDIATE 8

Methyl 11α-([N-2,2,2-trichloroethoxycarbonyl]-3-methylbutylamino)-3-oxo-5α-androstane-17β-carboxylate Pyridine (2.51 ml) then 2,2,2-trichloroethyl chloroformate (2.26 ml) were added to a stirred solution of methyl 11α-(3-methylbutylamino)-3-oxo-5α-androstane-17β-carboxylate (1.30 g) in dichloromethane (30 ml). The mixture was stirred for 3 h. It was then diluted with dichloromethane (75 ml) and successively washed with 2M-HCl (2×), 5% NaHCO$_3$ solution (2×) and water then dried and evaporated to a solid. This was purified by column chromatography eluted with ethyl acetate/petrol (1:3) to give a foam (1.70 g). A portion was crystallised from ethanol-water (15:4) to give the title compound, m.p. 104°–106° C., $[α]_D$+67°.

INTERMEDIATE 9

Methyl 3α-hydroxy-11α-([N-2,2,2-trichloroethoxycarbonyl]-3-methylbutylamino)-5α-androstane-17β-carboxylate A solution of Intermediate 8 (1.00 g) in chloroiridic acid reagent (15 ml) was heated at reflux for 3¾h. The cooled solution was diluted with dichloromethane (50 ml) and successively washed with M-HCl, 5% NaHCO$_3$ solution and water then dried and evaporated to a foam (954 mg). This was purified by column chromatography eluted with chloroform-ethanol (98:2) to give a white foam (858 mg). The bulk of this (812 mg) was further purified by preparative t.l.c. using ethyl acetate/petrol (1:3) to give the title compound (484 mg), $[α]_D$+59°.

INTERMEDIATE 10

Methyl 3α-ethoxy-11α-([N-2,2,2-trichloroethoxycarbonyl]-3-methylbutylamino)-5α-androstane-17β-carboxylate A mixture of Intermediate 9 (595 mg), silver oxide (3.57 g) and ethyl iodide (25 ml) was heated under reflux for 23 h then cooled and filtered. The filter pad was washed with ether (25 ml) and the combined filtrate and washings were evaporated to a foam (618 mg). This was subjected to preparative t.l.c. using ethyl acetate/petrol (1:3) to give the title compound (175 mg), $[α]_D$+54°.

INTERMEDIATE 11

Methyl 3α-hydroxy-11α-(3-methylbutylamino)-5α-androstane-17β-carboxylate hydrochloride 3-Methylbutanal (2.62 ml) and sodium cyanoborohydride (306 mg) were added to a solution of methyl 11α-amino-3α-hydroxy-5α-androstane-17β-carboxylate (5.77 g) in ethanol (130 ml) and after 18 h sodium borohydride (0.7 g) was added. After a further 15 minutes water (350 ml) was added and the mixture was extracted with ether (×2). The extract was washed with water, dried (Na$_2$SO$_4$) and evaporated to leave a foam which was dissolved in ethyl acetate (200 ml). Concentrated hydrochloric acid solution (4 ml) was added to the stirred solution and the mixture was diluted with ether (200 ml). The solid formed was collected by filtration, dried and stirred with ethyl acetate (100 ml) for 0.5 h. The solid was collected and dried to give the title compound (4.82 g) m.p. dec 230°–300° C., $[α]_D$+30°.

INTERMEDIATE 12

Methyl 3β-hydroxy-11α-[(N-benzyloxycarbonyl)-3-methylbutylamino]-5α-androstane-17β-carboxylate Benzyl chloroformate (1.7 g) was added to a stirred mixture of methyl 3β-hydroxy-11ζ-(3-methylbutylamino)-5α-androstane-17β-carboxylate hydrochloride (2 g) and sodium carbonate (1 g) in dioxan (70 ml) and water (20 ml). After 20 minutes the mixture was diluted with water (200 ml) and extracted with ethyl acetate (2×). The extract was washed with water, dried and evaporated to an oil (3.2 g) which was purified by column chromatography on silica eluted with chloroform/methanol (19:1) to give the title compound (2 g).

INTERMEDIATE 13

Methyl 3α-benzoyloxy-11α-[(N-benzyloxycarbonyl)-3-methylbutylamino]-5α-androstane-17β-carboxylate Diethyl azodicarboxylate (348 mg) in dry tetrahydrofuran (3 ml) was added to a stirred mixture of benzoic acid (244 mg), triphenylphosphine (524 mg) and Intermediate 12 (544 mg) in dry tetrahydrofuran (7 ml). After 1 h water (100 ml) was added and the mixture was extracted with ether (2×). The extract was washed with wafter (50 ml), dried and evaporated to an oil (1.7 g) which was purified by column chromatography on silica eluted with chloroform and preparative t.l.c. in chloroform to give the title compound (237 mg). $[α]_D$+90°.

EXAMPLE 1

Methyl 2β,3α-diethoxy-11α-(3-methylbutylamino)-5α-androstane-17β-carboxylate

Sodium cyanoborohydride (770 mg) and 3-methylbutanal (1.0 ml) were added to a stirred solution of Intermediate 6 (770 mg) in ethanol (15 ml) and the mixture was stirred for 20 h. The mixture was diluted with 5% NaHCO$_3$ solution (50 ml) and extracted with ether (3×). The extract was washed with water (1×), dried and evaporated to give an oil. This was purified by preparative t.l.c. (chloroform/methanol (9:1)) to give the title compound (505 mg), $[\alpha]_D+21.3°$, $\nu_{max}$ 1724 cm$^{-1}$.

EXAMPLE 2

Ethyl 3α-acetoxy-11α-(3-methylbutylamino)-2β-ethoxy-5α-androstane-17β-carboxylate Ethyl 2β-ethoxy-3α-hydroxy-11α-(3-methylbutylamino)-5α-androstane-17β-carboxylate (200 mg) in chloroform (2.15 ml) containing dry toluene-4-sulphonic acid (PTSA; 172 mg) was stirred for 20 min, then treated with acetic anhydride (0.5 ml) and the mixture left for 18 h. The reaction mixture was diluted with ethanol and evaporated. The residue in ethyl acetate was washed with dilute ammonia solution (2×) and water (1×), dried and evaporated to give the title compound as an oil (220 mg), $[\alpha]_D+25.8°$ (CHCl$_3$ C=1%), $\nu_{max}$ 1720 cm$^{-1}$.

EXAMPLE 3

Methyl 3α-acetoxy-11α-(3-methylbutylamino)-2β-ethoxy-5α-androstane-17β-carboxylate Methyl 2β-ethoxy-3α-hydroxy-11α-(3-methylbutylamino)-5α-androstane-17β-carboxylate (464 mg) in chloroform containing dry PTSA (344 mg) was stirred for 20 min, then treated with acetic anhydride (1.0 ml) and the mixture left for 3 h. The reaction mixture was diluted with ethanol and evaporated to give an oil. This was dissolved in ethyl acetate, washed with dilute ammonia solution (2×), water (1×), dried and evaporated to give an oil. This was purified by preparative t.l.c. in CHCl$_3$/MeOH (20:1) to give the title compound as an oil (415 mg), $[\alpha]_D+27.9°$, $\nu_{max}$ 1725 cm$^{-1}$.

EXAMPLE 4

Methyl 3α-acetoxy-11α-cyclohexylamino-2β-methoxy-5α-androstane-17β-carboxylate Methyl 11α-cyclohexylamino-3α-hydroxy-5α-androstane-17β-carboxylate (740 mg) in chloroform (8 ml) containing dry PTSA (640 mg) was stirred for 20 min then treated with acetic anhyride (1.9 ml) and left for 20 h. The reaction mixture was diluted with ethanol and evaporated to give an oil. This was dissolved in ethyl acetate, washed with dilute ammonia solution (2×) and water (1×), dried and evaporated to give a foam. This was purified by preparative t.l.c. in chloroform/methanol (9:1) to give a foam which was crystallised from acetonitrile to give the title compound, m.p. 87°–89° $[\alpha]_D+16.9°$.

EXAMPLE 5

Methyl 11α-cyclohexylamino-2β,3α-diacetoxy-5α-androstane-17β-carboxylate

Methyl 2β-acetoxy-11α-cyclohexylamino-3α-hydroxy-5α-androstane-17β-carboxylate (1.156 g) in chloroform (12.5 ml) containing dry PTSA (1.0 g) was stirred for 20 min. then treated with acetic anhydride (2.9 ml) and the mixture left for 18 h. The mixture was diluted with ethanol and evaporated to give an oil. This was dissolved in ethyl acetate, and washed with dilute ammonia solution (1×) water (1×), dried and evaporated under reduced pressure to give a foam. This was purified by preparative t.l.c. in chloroform/methanol (9:1) to give the title compound (790 mg), $[\alpha]_D+36.8°$, $\nu_{max}$ 1724 cm$^{-1}$.

EXAMPLE 6

Methyl 2β,3α-diacetoxy-11α-(3-methylbutylamino)-5α-androstane-17β-carboxylate Methyl 2β-acetoxy-3α-hydroxy-11α-(3-methylbutylamino)-5α-androstane-17β-carboxylate (3.069 g) in chloroform (33 ml) containing dry PTSA (2.64 g) was stirred for 20 min then treated with acetic anhydride (6.5 ml) and the mixture left for 5 h. The mixture was diluted with ethanol and evaporated to give an oil. This was dissolved in ethyl acetate, washed with aqueous ammonia solution (2×) and water (1×), dried and evaporated to give an oil (2.867 g). This was purified by preparative t.l.c. in chloroform/methanol (9:1) to give the title compound $[\alpha]_D+48.6°$, $\nu_{max}$ 1730 cm$^{-1}$.

EXAMPLE 7

Methyl 3α-acetoxy-11α-cyclohexylamino-5α-androstane-17β-carboxylate

Methyl 11α-cyclohexylamino-3α-hydroxy-5α-androstane-17β-carboxylate (550 mg) in chloroform (5.5 ml) containing dry PTSA (440 mg) was stirred for 20 min then treated with acetic anhydride (1.0 ml) and left for 18 h. The reaction mixture was diluted with ethanol and evaporated to give an oil. The residue is ethanol (10 ml) was diluted with 5% NaHCO$_3$ solution (50 ml) and water (100 ml) and extracted with ether (3×). The extracts were washed with water (1×), dried and evaporated to give an oil. This was crystallised from methanol to give the title compound (249 mg), m.p. 126°–128°, $[\alpha]_D+12°$.

EXAMPLE 8

Methyl 3α-ethoxy-11α-(3-methylbutylamino)-5α-androstane-17β- carboxylate

A mixture of Intermediate 10 (970 mg), zinc dust (2.5 g) and glacial acetic acid (25 ml) was stirred for 5 h then filtered through a glass fibre pad using chloroform (50 ml) as washings. The combined filtrate and washings were evaporated to an oil which was partitioned between ethyl acetate (50 ml) and 0.5 M-HCl (100 ml). The layers were separated and the aqueous portion extracted with further ethyl acetate (50 ml). The combined organic portions were washed with 5% NaHCO$_3$ solution and brine then dried and evaporated to give a colourless oil (629 mg). This was purified by column chromatography eluted with chloroform-ethanol (19:1) to give the title compound (499 mg), $[\alpha]_D+20.5°$, $\nu_{max}$ 1722 cm$^{-1}$.

EXAMPLE 9

Methyl 3α-acetoxy-11α-(3-methylbutylamino)-5α-androstane-17β-carboxylate

A solution of toluene-4-sulphonic acid in chloroform (80 mg/ml, 2 ml) was added to a solution of Intermediate 11 (300 mg) in chloroform (5 ml). Acetic anhydride (0.5 ml) was added and the mixture was left for 4 h.

Ethanol (10 ml) was added and the mixture was evaporated to leave an oil. This procedure was repeated twice and the residue was treated with 5% NaHCO₃ solution (10 ml). The oily precipitate was extracted with ether (2×) and the extract was washed with water, dried and evaporated to leave an oil which was purified by preparative t.l.c. in CHCl₃:methanol (9:1) to give the title compound (229 mg), $[\alpha]_D +25°$, $\nu_{max}$ 1725 cm$^{-1}$ (c=o).

EXAMPLE 10

Methyl 3α-benzoyloxy-11α-(3-methylbutylamino)-5α-androstane-17β-carboxylate

A solution of Intermediate 13 (207 mg) in methanol (30 ml) was hydrogenated over 10% palladium on carbon (50 mg) for 3 h. The catalyst was removed by filtration and washed with methanol (5 ml). The filtrate and washings were evaporated to leave an oil which was dissolved in ethyl acetate and filtered. The filtrate was evaporated to leave an oil (182 mg) which was purified by preparative t.l.c. in ethyl acetate/petrol (1:2) to give the title compound (57 mg). $[\alpha]_D +48.0°$.

EXAMPLES 11-19

Table 1 summarizes the preparation of the hydrochloride salts.

A 0.0979M solution of hydrochloric acid in water was added to the base or a suspension of the base in any additional water until either a clear solution was obtained or no more base dissolved. The mixture was made up to the appropriate weight or volume with water and filtered and any undissolved base was collected, dried and weighed to determine the solution concentration. The pH was measured.

TABLE 1

| Example No. | Example No. of Free base | Wt. (mg) | Vol HCl (ml) | Additional Water (ml) | Total wt. or Vol. | Solid residue (mg) | pH | Conc'n (%) |
|---|---|---|---|---|---|---|---|---|
| 11 | 1 | 100 | 2.08 | — | 10 g | — | 3.0 | 1 |
| 12 | 2 | 100 | 4.0 | 18 | 25 g | 30.0 | 2.0 | 0.28 |
| 13 | 3 | 105 | 2.15 | 6 | 10 g | — | 2.6 | 1.05 |
| 14 | 4 | 100 | 2.04 | — | 20 g | — | 3.8 | 0.5 |
| 15 | 5 | 100.7 | 1.93 | — | 20 g | 3.9 | 3.4 | 0.48 |
| 16 | 6 | 100.1 | 1.97 | — | 20 g | 7.7 | 3.4 | 0.46 |
| 17 | 7 | 100 | 2.16 | — | 10 ml | — | 3.1 | 1 |
| 18 | 8 | 100 | 2.26* | 5 | 10 g | — | 2.7 | 1 |
| 19 | 9 | 205 | 4.5* | — | 20 g | 6 | 2.2 | 1 |

*0.0987 M HCl

The following Examples illustrate pharmaceutical formulations of the compounds according to the invention.

EXAMPLE A

| Tablet - Wet granulated | mg/tablet |
|---|---|
| Methyl 3α-acetoxy-2β-ethoxy-11α-(3-methylbutylamino)-5α-androstane 17β-carboxylate hydrochloride | 108.00 |
| Maize starch | 138.0 |
| Polyvinyl pyrrolidone | 2.5 |
| Sodium starch glycolate | 7.5 |
| Magnesium stearate | 2.0 |
| Tablet weight | 258.00 |

Sieve the steroid and maize starch through a 40 mesh screen. Blend the maize starch with the steroid in a suitable blender. Make a 5–10% w/v aqueous solution of the polyvinyl pyrrolidone. Add this solution to the mixing powder and mix until granulated. Pass the granulate through a number 12 screen. Dry the granules at 50° C. in an oven or in a fluid bed dryer. Screen the dry granules through a 16 mesh screen, and blend in the sodium starch glycolate and magnesium stearate previously sieved through a 60 mesh screen. Compress on appropriate punches on an automatic tablet machine. The tablets may be coated with a thin polymeric coat applied by the usual techniques. The film coat may contain a pigment.

EXAMPLE B

| Intravenous Injection | % w/v |
|---|---|
| Methyl 3α-acetoxy-2β-ethoxy-11α-(3-methylbutylamino)-5α-androstane 17β-carboxylate hydrochloride | 0.1–1.0 |
| Sodium metabisulphite | 0.1 |
| Sodium citrate BP | 0.1 |
| Citric acid monohydrate BP | 0.05 |
| Sodium chloride | 0.7 |
| Water for Injection to | 100 |

METHOD OF MANUFACTURE

Dissolve the steroid hydrochloride in approximately half the total volume of Water for Injection. Add the sodium metabisulphite, sodium citrate, sodium chloride and citric acid and stir to dissolve. Make the solution up to the final volume using more Water for Injection. Filter the solution through a 0.22 membrane and fill aseptically into the final sterilized containers.

We claim:

1. Compounds of the formula

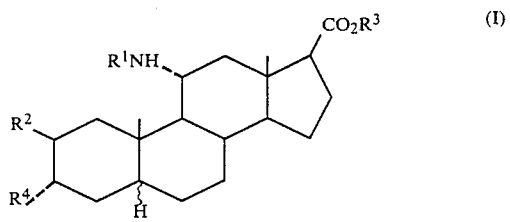

wherein
R¹ is a C₃₋₈ alkyl group or a C₃₋₇ cycloalkyl group;
R² is a hydrogen atom, a C₁₋₆ alkoxy group or a C₂₋₅ alkanoyloxy group;
R³ is a C₁₋₆ alkyl group or a C₃₋₇ cycloalkyl group; and
R⁴ is a group —OR⁵ or —OCOR⁶ where
R⁵ is an alkyl or alkenyl group which may contain up to 6 carbon atoms (or such a group substituted by halogen, C₁₋₆ alkoxy, carboxy, phenyl, phenyl substituted by nitro, halo, C₁₋₄ alkoxy or C₁₋₄ alkyl), a C₃₋₇ cycloalkyl group, a phenyl group (or such a group substituted by nitro, halo, C₁₋₄ alkoxy or C₁₋₄ alkyl), or a carbon-attached 5–7 membered heterocyclic ring in which the heteroatom is selected from nitrogen, oxygen and sulphur, and
R⁶ is a hydrogen atom or a group R⁵ as defined above;
provided that when the compounds contain a 5β-hydrogen atom, R² is a hydrogen atom;
and salts thereof.

2. Compounds as claimed in claim 1 wherein R¹ is an isopentyl, hexyl, isohexyl, neohexyl, cyclopentyl or cyclohexyl group.

3. Compounds as claimed in claim 1 wherein $R^3$ is a methyl or ethyl group.

4. Compounds as claimed in claim 1 wherein $R^4$ is a methoxy, ethoxy or acetoxy group.

5. Compounds as claimed in claim 1 having a 5α-hydrogen atom.

6. Compounds as claimed in claim 1 in the form of physiologically acceptable acid addition salts.

7. Compounds as claimed in claim 6 in the form of hydrochloride, hydrobromide, phosphate, sulphate, p-toluenesulphonate, methanesulphonate, citrate, tartrate, acetate, ascorbate, lactate, maleate, succinate, tricarballylate, glutarate and glutaconate acid addition salts.

8. Compounds of formula (I) as claimed in claim 1 selected from:
(a) ethyl 3α-acetoxy-2β-ethoxy-11α-(3-methylbutylamino)-5α-androstane-17β-carboxylate;
(b) methyl 3α-acetoxy-2β-ethoxy-11α-(3-methylbutylamino)-5α-androstane-17β-carboxylate;
(c) methyl 2β,3α-diethoxy-11α-(3-methylbutylamino)-5α-androstane-17β-carboxylate;
(d) methyl 11α-cyclohexylamino-2β,3α-diacetoxy-5α-androstane-17β-carboxylate;
(e) methyl 3α-acetoxy-11α-cyclohexylamino-5α-androstane-17β-carboxylate;
(f) methyl 3α-acetoxy-11α-cyclohexylamino-2β-methoxy-5α-androstane-17β-carboxylate;
(g) methyl 2β,3α-diacetoxy-11α-(3-methylbutylamino)-5α-androstane-17β-carboxylate;
(h) methyl 3α-acetoxy-11α-(3-methylbutylamino)-5α-androstane-17β-carboxylate;
(i) methyl 3α-ethoxy-11α-(3-methylbutylamino)-5α-androstane-17β-carboxylate;
and their physiologically acceptable acid addition salts.

9. Compounds as claimed in claim 8 in the form of their hydrochlorides.

10. Pharmaceutical compositions comprising at least one compound of formula (I) as claimed in claim 1 or a physiologically acceptable salt thereof in admixture with one or more pharmaceutical carriers or excipients.

11. A method of therapy or prophylaxis of a human or animal body suffering from or liable to cardiac dysrhythmias which method comprises administering to the said body an effective amount of a compound of formula (I), or a physiologically acceptable salt thereof as claimed in claim 1.

12. Compounds as claimed in claim 1 wherein $R^2$ is a hydrogen atom or a methoxy, ethoxy or propoxy group.

13. Compounds of the formula

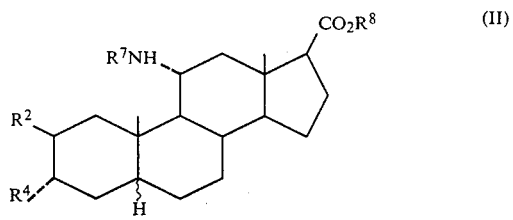

wherein
$R^7$ is a hydrogen atom, a $C_{3-8}$ alkyl group or a $C_{3-7}$ cycloalkyl group;
$R^8$ is a hydrogen atom, a $C_{1-6}$ alkyl group or a $C_{3-7}$ cycloalkyl group; and
$R^2$ is a hydrogen atom, a $C_{1-6}$ alkoxy group or a $C_{2-5}$ alkanoyloxy group; and
$R^4$ is a group —$OR^5$ or —$OCOR^6$ where
$R^5$ is an alkyl or alkenyl group which may contain up to 6 carbon atoms (or such a group substituted by halogen, $C_{1-6}$ alkoxy, carboxy, phenyl, phenyl substituted by nitro, halo, $C_{1-4}$ alkoxy or $C_{1-4}$ alkyl), a $C_{3-7}$ cycloalkyl group, a phenyl group (or such a group substituted by nitro, halo, $C_{1-4}$ alkoxy or $C_{1-4}$ alkyl), or a carbon-attached 5-7 membered heterocyclic ring in which the heteroatom is selected from nitrogen, oxygen and suplhur, and
$R^6$ is a hydrogen atom or a group $R^5$ as defined above;
with the provisos that at least one of $R^7$ and $R^8$ is a hydrogen atom and that when the compounds contain a 5β hydrogen atom $R^2$ is a hydrogen atom;
and salts thereof.

14. Compounds as claimed in claim 2 wherein
$R^2$ is a hydrogen atom or a methoxy, ethoxy or propoxy group;
$R^3$ is a methyl or ethyl group; and
$R^4$ is a methoxy, ethoxy or acetoxy group.

15. Compounds as claimed in claim 14 having a 5α-hydrogen atom.

* * * * *